United States Patent [19]

Scozzie

[11] 3,965,139
[45] June 22, 1976

[54] 2-CHLORO-N-(CYANOMETHYL)ACETANILIDES

[75] Inventor: James A. Scozzie, Wickliffe, Ohio

[73] Assignee: Diamond Shamrock Corporation, Cleveland, Ohio

[22] Filed: May 1, 1974

[21] Appl. No.: 465,755

Related U.S. Application Data

[63] Continuation-in-part of Ser. No. 316,409, Dec. 18, 1972, abandoned.

[52] U.S. Cl............................. 260/465 D; 71/105
[51] Int. Cl.² ...................................... C07C 121/78
[58] Field of Search ............... 260/465 D, 562 B

[56] References Cited

UNITED STATES PATENTS 3,247,206  4/1966  Yost et al. .................... 260/465 X
3,535,377  10/1970  Steinbrunn et al. ............... 260/562

Primary Examiner—Lewis Gotts
Assistant Examiner—Dolph H. Torrence
Attorney, Agent, or Firm—Helen P. Brush

[57] ABSTRACT

A series of 2-chloro-N-(cyanomethyl)acetanilide compounds are active as selective herbicides for protecting certain crops against infestation by undesirable grasses.

1 Claim, No Drawings

2-CHLORO-N-(CYANOMETHYL)ACETANILIDES

BACKGROUND OF THE INVENTION

This application is a continuation-in-part of my copending application, Ser. No. 316,409, filed Dec. 18, 1972, now abandoned.

This invention relates to a group of 2-chloro-N-(cyanomethyl)acetanilides having herbicidal activity, particularly as selective herbicides for agronomic crops such as corn, sorghum, soybeans, cotton, and the like, and to their preparation. This invention further relates to herbicidal compositions and to methods for controlling or modifying the growth of plant systems.

It is known from U.S. Pat. No. Re. 26,961 that an N-alkyl-α-chloroacetanilide is useful as the active ingredient of a herbicide. Also, it is known from U.S. Pat. No. 3,442,945 that a 2-chloro-N-(methoxymethyl)acetanilide has useful herbicidal properties. Further, N-butyn-(1)-yl-(3)chloroacetanilide is known to be herbicidally active as set forth in U.S. Pat. No. 3,535,377.

I have now found that a group of 2-chloro-N-(cyanomethyl)acetanilides likewise possess good herbicidal properties, being effective for selectively controlling undesirable plant growth in certain agronomic crops, particularly when applied to newly seeded crop areas.

SUMMARY OF THE INVENTION

Accordingly, the present invention generally is directed to herbicidally-active 2-chloro-N-(cyanomethyl)acetanilides corresponding to the structural formula:

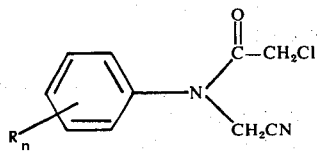

wherein $n$ is an integer of 1 or 2; and R is either $C_{1-3}$ alkyl, halogen, i.e., Cl or F, or a $C_{1-2}$ alkoxy radical.

These compounds are effective particularly as pre-emergence herbicides for the control of monocotyledonous plant species such as grassy-type weeds, without causing undesirable injury to the crops.

DESCRIPTION OF PREFERRED EMBODIMENTS

Specific 2-chloro-N-(cyanomethyl)acetanilide compounds of this invention include the following:
2-chloro-N-cyanomethyl-2',6'-diethylacetanilide
2-chloro-N-cyanomethyl-2'-methylacetanilide
2-chloro-N-cyanomethyl-2'-ethylacetanilide
2-chloro-N-cyanomethyl-2'-ethyl-6'-methylacetanilide
2-chloro-N-cyanomethyl-2',6'-dimethylacetanilide
2,4'-dichloro-N-cyanomethyl-2'-methylacetanilide
2-chloro-N-cyanomethyl-2'-fluoroacetanilide
2-chloro-N-cyanomethyl-2'-methyl-6'-isopropylacetanilide
2-chloro-N-cyanomethyl-2'-methoxyacetanilide
2,2'-dichloro-N-(cyanomethyl)acetanilide
2-chloro-N-cyanomethyl-3'-methylacetanilide
2-chloro-N-cyanomethyl-4'-fluoroacetanilide
2-chloro-N-cyanomethyl-2'-isopropylacetanilide
2-chloro-N-cyanomethyl-2',6'-diisopropylacetanilide
2'-bromo-2-chloro-N-(cyanomethyl)acetanilide
2-chloro-N-cyanomethyl-2'-ethoxyacetanilide
2,2'-dichloro-N-cyanomethyl-6'-methylacetanilide.

The compounds of the invention may be simply prepared by reacting the appropriate substituted N-cyanomethylaniline with at least a stoichiometric amount of either chloroacetic acid anhydride or chloride, usually in a suitable solvent medium, for a time period 2–10 hours and typically at the reflux temperature of the reaction mixture. The reaction further is conducted in the presence of an acid scavenger or, alternatively, the product mixture is washed well with the scavenger. The 2-chloro-N-(cyanomethyl)acetanilide product is purified by vacuum distillation or by recrystallization from a suitable solvent.

Some of the N-cyanomethylaniline intermediates employed to prepare the compounds of this invention are known compounds which, however, are not commercially available. Others of the intermediates have not been reported previously in the literature. All of these substituted N-cyanomethylaniline compounds may be prepared by reacting the appropriate substituted aniline with approximately a stoichiometric amount of chloroacetonitrile in a suitable solvent and under alkaline conditions. Alternatively, the substituted aniline and the chloroacetonitrile may be reacted in the absence of solvent and under nonalkaline conditions by utilizing a large excess of the aniline, i.e., 3–4 moles per each mole of the chloroacetonitrile. This reaction route is preferable due to the shorter reaction time possible and also because the formation of undesirable N,N-dicyanomethylaniline byproducts is minimized. Representative preparations of the N-cyanomethylaniline intermediates by each of the aforedescribed routes are given below.

The 2-chloro-N-(cyanomethyl)acetanilide compounds of this invention are either oily liquids or crystalline solids which generally have less than 5 percent solubility in water and varying degrees of solubility in many common organic solvents.

Reference may also be made to the examples for a fuller understanding of the invention. The infrared spectrum for each product described below is consistent with the assigned structure. All percentages, parts and/or quantities given other than volume proportions are by weight unless otherwise indicated.

EXAMPLE 1

A. Preparation of 2,6-Diethyl-N-cyanomethylaniline Intermediate

A reactor equipped with a thermometer, stirrer, $N_2$ inlet and outlet tubes and reflux condenser fitted with a drying tube is charged with 74.5 g (0.5 mole) of 2,6-diethylaniline, 37.8 g (0.5 mole) of chloroacetonitrile, 50.5 g (0.5 mole) of triethylamine, 60 g of acetonitrile, and 3.7 g of sodium iodide. The mixture is refluxed for 132 hours under slight positive $N_2$ pressure. The reaction mixture is cooled and poured into 800 ml of ice water. The supernatent organic layer which develops is isolated and dried over anhydrous magnesium sulfate. The mixture is then filtered and the volatiles are stripped in vacuo. The residue is vacuum distilled. The product obtained (17.6 g) is identified as 2,6-diethyl-N-cyanomethylaniline by elemental analysis. It has a boiling point of 105° C at 0.5 mm Hg pressure.

B. Preparation of
2-Chloro-N-cyanomethyl-2',6'-diethylacetanilide

The product solution is evaporated under vacuum, distilled to recover the aniline product. Using this procedure, results are as follows:

TABLE 1

| Example | Product | Reaction Temp. - °C | Reaction Time - hrs | Boiling Point °C/mm Hg | % Yield |
|---|---|---|---|---|---|
| 2 | N-cyanomethyl-3-methylaniline | 55–60 | 7 | 126–7 0.05–0.07 | 70 |
| 3 | N-cyanomethyl-2-ethylaniline | 50–55/ 80–85 | 5.5/5 | 127–9 0.06–0.07 | 51 |
| 4 | N-cyanomethyl-2,6-dimethylaniline | Reflux | 6 | 107–10/* 0.07–0.08 | 51 |
| 5 | N-cyanomethyl-2-isopropylaniline | Reflux 115–20 | 6/7 | 125–30/ 0.08 | 27 |
| 6 | 2-bromo-N-cyano-methylaniline | 125–130 | 5.5 | 109–15/ 0.04–0.05 | 55 |
| 7 | N-cyanomethyl-2,6-diisopropylaniline | Reflux/ 115–20 | 6/7 | 123–7/ 0.08 | 39 |

*Converted to white solid upon standing.

A reactor is charged with 3.8 g (0.02 mole) of the above-prepared 2,6-diethyl-N-cyanomethylaniline, 50 ml of ethyl acetate, and 3.5 g (0.02 mole) of chloroacetic anhydride. This reaction mixture is heated at reflux for 1.5 hours, after which another 0.02 mole of chloroacetic anhydride is added. After an additional 1.5 hours reaction, the solvent is stripped from the mixture in vacuo. The residue solidifies on standing. This is recrystallized from cyclohexane-petroleum ether, yielding 3.6 g of a cream-colored solid, melting at 62°–65° C. This is identified as 2-chloro-N-cyanomethyl-2',6'-diethylacetanilide by elemental and infrared analyses.

EXAMPLES 2–7

Other substituted N-cyanomethylaniline intermediates employed in this invention and which are novel compounds are prepared following the general procedure outlined above, except that no solvent or amine base is used. Likewise, the molar ratio of the substituted aniline reactant to the chloroacetonitrile is approximately 4:1. Following reaction, the semi-solid reaction mixture, in each instance, is mixed with pet ether and filtered. The filtrate is then dried over anhydrous sodium sulfate which is removed by filtration.

EXAMPLES 8–15

Following the general procedure as outlined in Example 1 above, other substituted N-(cyanomethyl)acetanilide compounds of this invention are prepared by reacting the appropriate N-cyanomethylaniline (e.g., products of Examples 2–7 above) with either chloroacetic acid anhydride or chloride. In each instance, benzene (50 ml) is employed as the solvent, and 0.1 m of the chloroacetic acid anhydride is used with 0.05 m of the aniline reactant. The reaction is conducted at the reflux temperature of the benzene for about 7.5 hours. The product is recovered in each instance by treating the reaction mixture with sodium carbonate solution, followed by drying over anhydrous sodium sulfate and filtering. Benzene is then vacuum stripped from the product solution. The white solid product is recovered by recrystallization from pet ether.

Table 2 below gives data for compounds prepared, including the melting point (°C), the % yield, and analysis as % C, H, and N for each compound.

TABLE 2

| Example | Product | % Yield | Melting Point °C | Elemental Analysis Calc. % | Found % |
|---|---|---|---|---|---|
| 8 | 2-chloro-N-cyanomethyl-3'-methylacetanilide | 97 | —[1] | C 59.3 H 4.9 N 12.6 | C 58.7 H 5.0 N 12.0 |
| 9 | 2,2'-dichloro-N-(cyanomethyl)acetanilide | 82 | 89–90 | C 49.4 H 3.3 N 11.5 | C 48.9 H 3.3 N 11.4 |
| 10 | 2-chloro-N-cyanomethyl-2',6'-dimethylacetanilide | 73 | 93–4 | C 60.9 H 5.5 N 11.8 | C 60.8 H 5.7 N 11.9 |
| 11 | 2-chloro-N-cyanomethyl-2'-isopropylacetanilide | 48 | 94–5 | C 62.3 H 6.1 N 11.2 | C 61.8 H 6.0 N 10.9 |
| 12 | 2-chloro-N-cyanomethyl-2',6'-diisopropyl-acetanilide | 68 | 130–1 | C 65.6 H 7.2 N 9.6 | C 65.2 H 7.4 N 9.4 |
| 13 | 2-chloro-N-cyanomethyl-2'-methoxyacetanilide | 75[2] | 71–2 | C 55.3 H 4.6 N 11.7 | C 55.3 H 4.6 N 11.7 |
| 14 | 2-chloro-N-cyanomethyl-2'-ethylacetanilide | 68[3] | 63–4 | C 60.9 H 5.5 N 11.8 | C 60.7 H 5.5 N 11.6 |
| 15 | 2'-bromo-2-chloro-N-(cyanomethyl)acetanilide | 53 | 80–1 | C 41.7 H 2.8 N 9.7 | C 41.6 H 2.6 N 10.0 |

[1]Brownish liquid product, boiling point not determined.
[2]Reaction time is 5.5 hours.
[3]Reaction time is 8.5 hours.

For herbicidal application, the compounds of the invention may be used in undiluted form. It is frequently desirable, however, to apply them in admixture with either liquid or solid inert, pesticidal carriers or adjuvants in the form of solutions, emulsions, suspensions, or dusts.

For the preparation of solutions for direct spraying, medium to high boiling mineral oil fractions, coal-tar oils, oils of vegetable and animal origin and polycyclic hydrocarbons such as naphthalene derivatives are suitable.

Aqueous formulations may be prepared by adding water to emulsifiable concentrates, pastes, or wettable powders of the active ingredient. Emulsions are prepared, e.g., by dissolving the active ingredient in a solvent and homogenizing the resulting solution in water by means of wetting or dispersing agents. Concentrates are prepared from active ingredient, emulsifying agent, and possibly solvent. Dusts (or wettable powders) are obtained by mixing or grinding the active ingredient with a solid carrier.

The herbicidal compositions of this invention may also contain other compatible growth regulants, fertilizers, spray oils, etc., according to common practice in herbicide formulating art at the present time. In general, the herbicidal compositions of the invention may contain from 0.01% to about 99% by weight of the N-(cyanomethyl)acetanilide compound as the active ingredient.

Plant growth is regulated by applying a herbicidally active amount of the N-(cyanomethyl)acetanilide to a newly seeded crop area. The compounds are particularly effective as preemergent grass herbicides when applied generally at rates ranging from about 0.5 to about 8 lb/A (pounds per acre), and, in most cases, provide satisfactory control when applied at rates from about 1 to about 2 lb/A.

EXAMPLE 16

Greenhouse Preemergence Herbicide Tests

To illustrate the preemergence herbicidal efficiency of the N-(cyanomethyl)acetanilides of this invention, test formulations are prepared of representative compounds by mixing 20 ml of an acetone solution containing 0.125 g of the test compound with 20 ml of water containing 0.01 g of Triton X-155 surfactant. The resultant formulations contain 3125 ppm of test compound, 50% by volume of acetone and 0.025% by weight of surfactant. Appropriate lower concentrations are obtained by diluting this formulation with surfactant-acetone solution so that the concentration of adjuvants is maintained at the original levels.

Seeds of three broadleaf and three grass species are planted in soil contained in 10 × 8 × 3 inch aluminum pans filled with 1.5 inches of composted soil. The broadleaf species are pigweed (*Amaranthus retroflexus*), a velvetleaf (*Abutilon theophrasti*), and morningglory (*Ipomea coccinea*); the grasses are red millet (*Panicum milliacem*), greenfoxtail (*Setaria viridis*) and Japanese millet (*Echinochloa frumentacea*).

The pans are then sprayed so that the soil surface is uniformly covered with dilutions of the stock formulation providing dosage rates of the test compounds corresponding to 8, 4, 2, 1, 0.5, and 0.25 lb/A. Two weeks after treatment, percent control (plant kill) at each dosage rate is estimated. The lowest concentration of each compound (lb/A) found to provide 50% or greater control of the grass weeds is as follows:

TABLE 3

| Test Compound | Minimum Dosage (lb/A) Providing at Least 50% Preemergence Control of Grass Species |
|---|---|
| Product of Ex. | |
| 1 | 0.50 |
| 8 | 0.50 |
| 9 | 0.50 |
| 10 | 0.25 |
| 11 | 1.00 |
| 12 | 0.50 |
| 13 | 0.50 |
| 14 | 0.50 |
| 15 | 1.00 |

No control of the broadleaf weed species is exhibited by any of the compounds at the test concentrations.

The above results indicate that the test compounds demonstrate good activity for controlling growth of the grass-type weed species tested at minimum dosage rates.

EXAMPLE 17

Field Preemergence Test

Test plots of fertilized, light sandy soil containing 0.7% organic matter are sprayed uniformly with aqueous suspensions prepared from an emulsifiable concentrate containing 12%, by weight, of 2-chloro-N-cyanomethyl-2',6'-diethylacetanilide (the product of Example 1) diluted to provide dosage rates of the test compound corresponding to 2, 1, 0.5, and 0.25 pound per acre (lb/A). The plots are then sown with seeds of the following crop plants: sweet corn, cotton (Coker 413), and soybeans, var. Davis. Seeds of the following weed plants are planted: redroot pigweed, prickly sida, and common lambsquarter (broadleaf species); goosegrass and giant foxtail (grass species).

Three to four weeks after planting, percent control (plant kill) of the test plants is estimated, from a rating of 0 which denotes no injury to the plant up to 100 which denotes complete destruction. The % weed control exerted by 2-chloro-N-cyanomethyl-2',6'-diethylacetanilide is as follows:

TABLE 4(A)

| Dosage rate of Compound lb/A | % Weed Control | | | | |
|---|---|---|---|---|---|
| | Broadleaves | | | Grasses | |
| | Redroot Pigweed | Prickly Sida | Lambsquarter | Goosegrass | Giant Foxtail |
| 2 | 90 | 40 | 88 | 99 | 82 |
| 1 | 55 | 12 | 60 | 95 | 65 |
| 0.5 | 33 | 0 | 20 | 88 | 27 |
| 0.25 | 0 | 0 | 0 | 63 | 0 |

Phytotoxic effects observed on the crop species is estimated with results as follows:

TABLE 4(B)

| Dosage Rate of Compound lb/A | % Crop Kill | | |
|---|---|---|---|
| | Corn | Cotton | Soybeans |
| 2 | 0 | 3 | 0 |
| 1 | 0 | 0 | 0 |

The above results indicate that the test compound provides good control of grassy-type weeds, and, surprisingly, also exerts significant herbicidal activity against two of the broadleaf species at a dosage rate of 2 lb/A. Both corn and soybeans are tolerant to the chemical at this dosage, while cotton exhibits minimal phytotoxicity effects.

EXAMPLE 18

This example illustrates the performance of 2-chloro-N-cyanomethyl-2',6'-diethylacetanilide in a different type soil than employed in the previous example. For this test, test plots of a loam-type, heavier soil containing 5.5% organic matter are sprayed uniformly with formulations of the test compound providing dosage rates of 4, 2, and 1 pound per acre (lb/A). The plots are then sown to cotton and soybeans and with seeds of the broadleaf, redroot pigweed, and the grasses, Johnson grass and yellow foxtail, as indicator weed plants.

Approximately three weeks after planting, the test plots are examined and percent control of plant growth is rated from 0% to 100% as previously described. The results obtained are as follows:

TABLE 5

| Dosage rate of Compound lb/A | % Control of Plant Growth |||||
|---|---|---|---|---|---|
| | Crops || | Weeds |||
| | Corn | Soybeans | Pigweed | Johnson-grass | Yellow Foxtail |
| 4 | 10 | 5 | 40 | 80 | 95 |
| 2 | 0 | 0 | 0 | 80 | 95 |
| 1 | 0 | 0 | 0 | 60 | 90 |

These data indicate that at dosage rates of 1–2 lb/A, the test compound is selective for controlling the grass species while being noninjurious to the corn and soybean stands. Likewise, in this heavy soil, the test compound shows no activity for controlling the broadleaf species at dosage rates of 1–2 lb/A. This result is much different than the good broadleaf weed control exhibited by the compound at these same dosage rates in a light, sandy soil.

I claim:
1. 2-Chloro-N-cyanomethyl-2',6'-dimethylacetanilide.

* * * * *